United States Patent [19]
Chen

[11] Patent Number: 5,804,453
[45] Date of Patent: Sep. 8, 1998

[54] FIBER OPTIC DIRECT-SENSING BIOPROBE USING A PHASE-TRACKING APPROACH

[75] Inventor: Duan-Jun Chen, 25 Hopewell Dr., Stoney Brook, N.Y. 11790

[73] Assignee: Duan-Jun Chen, Akron, Ohio

[21] Appl. No.: 599,298

[22] Filed: Feb. 9, 1996

[51] Int. Cl.[6] .................................................. G01N 33/543
[52] U.S. Cl. .......................... 436/518; 436/501; 435/176; 422/82.07; 424/130.1; 424/137.1; 356/345; 385/12
[58] Field of Search .......................... 435/176; 422/82.07; 350/96.29; 436/501, 518; 424/130.1–137.1; 356/345; 385/12

[56] References Cited

U.S. PATENT DOCUMENTS 5,077,210  12/1991  Eigler et al. .

OTHER PUBLICATIONS

"Webster's II New Riverside Dictionary" p. 1212 Houghton Mifflin Company USA, 1994.

Ogert et al., "Detection of Clostridium botulinum Toxin A Using a Fiber Optic–Based Biosensor", Analytical Biochemistry, vol. 205, 1992, pp. 306–312, 1992.

Brecht et al., "Direct monitoring of Antigen–Antibody Interactions by Spectral Interferometry", Sensors and Actuators, vol. B6, 1992, pp. 96–100, 1992.

Brecht, A. et al., "Direct monitoring of antigen–antibody interactions by spectral interferometry", Sensors and Actuators, vol. B6 (1992); pp. 96–100.

Brecht, A. et al., "Interferometric immunoassay in a FIA–System: a sensitive and rapid approach in label–free immunosensing", Biosensors & Bioelectronics, vol. 8 (1993), pp. 387–392.

Brecht, A. et al., "Theoretical and Experimental Detectivity of the RIFS—transducer in Affinity–sensing", Biosensors 94, The Third World Congress on Biosensors: Abstracts, Oral Session, (Jun. 2, 1994), p. 68.

Weber, A. et al., "Fiber–optic fluorimetry in biosensors: comparison between evanescent wave generation and distal–face generation of fluorescent light", Biosensors & Bioelectronics, vol. 7, (1992) pp. 193–197.

Boiarski, A. et al., "Integrated–optic biosensor", SPIE, Fiber Optic Sensors in Medical Diagnostics, vol. 1886 (1993) pp. 15–26.

Fabricius, N. et al., "A gas sensor based on an integrated optical Mach–Zehnder interferometer", Sensors and Actyators, vol. B7 (1992) pp. 672–676.

Cao. L. et al., "Detection of *Yersinia pestis* Fraction 1 Antigen with a Fiber Optic Biosensor", Journal of Clinical•Microbiology, vol. 33 No. 2, (Feb. 1995), pp. 336–341.

Rudraraju, S. et al., "Acoustic wave propagation in composite materials: an experimental study", SPIE, vol. 2191, (Jul. 1994) pp. 487–493.

Jorgenson, R. et al., "A Novel Surface Plasmon Resonance BAsed Fiber Optic Sensor Applied to Biochemical Sensing", SPIE, vol. 1886 (1993) pp. 35–48.

Lukosz, W. et al., "Output grating coulers on planar optical waveguides as direct immunosensors", Biosensors & Bioelectronics, vol. 6 (1991) pp. 227–232.

Kimoshita, Y. et al., "Sensing of Herbicide Residues using Surface Plasmon Resonance Technique", The Third World Congress on Biosensors: Abstracts, (1994) p. 257.

Lundstrom, I., et al. "Immunosensors Based on Surface Plasmon Resonance", The Third World Congress on Biosensors: Abstracts, (1991), p. 91.

Daview, R. et al., "An Optical Biosensor System for Molecular Interaction Studies", American Biotechnology Laboratory, (Jul. 1993).

Schneider, I. et al., "Herbicide Detection using Reaction, Centers Integrated into Liposomes Binding to Grating Couplers", The Third World Congress on Biosensors: Abstracts, (1994) p. 271.

Tiefenthaler, K. "Grating Couplers as Label–free Biochemical Waveguide Sensors", Biosensors & Bioelectronics, vol. 8, No. 7–8, pp. xxxv–xxxvii (1993).

*Primary Examiner*—Paula K. Hutzell
*Assistant Examiner*—Heatha A. Bakalyar
*Attorney, Agent, or Firm*—Michaelson & Wallace; Peter L. Michaelson; John C. Pokotylo

[57] ABSTRACT

A fiber optic bioprobe in which an immobilized biolayer, such as an antigen or antibody, acts as a sensing etalon of a Fabry-Perot interferometer. The bioprobe is used in a system in which a shift in the spectral dispersion pattern, caused by reflected out-of-phase beams, is used to determine a concentration of a substance in a sample solution.

21 Claims, 12 Drawing Sheets

FIBER OPTIC DIRECT-SENSING BIOPROBE USING A PHASE-TRACKING APPROACH

BACKGROUND OF THE INVENTION a. Field of the Invention

My invention concerns a biosensor which uses a bioprobe for detecting the presence of a particular biologic (or chemical) material. More specifically, my invention concerns a fiber optic bioprobe in which an immobilized (e.g., coated or disposed) biolayer, such as an antigen or antibody, for example, acts as a sensing etalon of a Fabry-Perot interferometer.

b. The Prior Art

Detecting whether or not a particular biologic material is present in a sample is often carried out for research and medical diagnostic purposes. For example, blood serum is often tested for the presence of a particular antibody. An antigen is a substance which specifically reacts with its complementary antibody and is therefore used, for example, to test blood serum for the presence or absence of its complementary antibody. The presence or absence of the antibody can be detected, for example, by methods of immunodiffusion, immunoelectrophoresis, and immunoflurescence, each of which is briefly described below.

Immunodiffusion is a serological procedure in which antigen and antibody solutions are permitted to diffuse, through a gel matrix, towards each other. An interaction between the antigens and their complementary antibodies is manifested by a precipitin line in each solution. Immunoelectrophoresis is a serological procedure in which components of an antigen are separated by electrophoretic migration and then made visible by immunodiffusion of specific antibodies. Immunoflorescence is a procedure used to identify an immune response. A particular antigen is stained (or "labeled") with a label that fluoresces in a light of a particular wavelength, for example, ultraviolet light, thereby permitting such an antigen can be easily identified. Other types of labels include radioisotope labels and enzyme labels.

One known methodology of exploiting immunoflorescense to identify a biologic material (such as an antibody or antigen) uses fiber optic fluorescent and chemi-luminescent biosensors. Such fiber optic biosensors are reportedly the largest group of fiber optic biosensors used both commercially, and in research and development. This known methodology can use two types of fiber optic biosensors; namely, sandwich fiber optic biosensors and displacement biosensors, each using a different reaction format. The use of sandwich type fiber optic biosensors is illustrated in FIGS. 1a and 1b while the use of displacement type fiber optic biosensors is illustrated in FIGS. 1c and 1d.

As shown in FIG. 1a, a sandwich type fiber optic biosensor is formed by immersing an optical fiber 100, having a reagent 102 (such as an antigen for example) coated on its distal end, into a solution 104 to be tested for the presence of antibodies 106 complementary with the reagent 102. If antibodies 106 complementary with the reagent 102 are present in the solution 104, they will bond with the reagent 102. The optical fiber 100 is kept immersed in the solution 104 for an appropriate incubation period and then is washed, for example, by saline.

As shown in FIG. 1b, the optical fiber 100 having the reagent 102 and any bonded antibodies 106, is then immersed into a solution having the reagent 110 (such as antigens for example). A label 112, such as a fluorescent indicator for example, is attached to the reagent 110. If any antibodies 106 are bonded to the reagent 102, the reagent 110, along with the label 112, will bond with such antibodies 106. The optical fiber 100 is then illuminated with a light source (not shown) at its proximal end. Any fluorescently labeled reagent 110 bonded to the antibodies 106, which are in turn bonded to the reagent 102 at the distal end of the optical fiber 100, will become excited by the light and will return a fluorescent signal. The resulting fiber optic biosensor will have adjacent layers of the reagent 102, the antibody 106, and the reagent 110 with label 112 at its distal end; hence the term "sandwich" type biosensor. In a fiber optic sandwich type biosensor, the higher the concentration of antibodies 106 in the test sample, the more labeled reagent 110 will bond to it, and therefore, the more intense the returned fluorescent signal.

As shown in FIG. 1c, a displacement type fiber optic biosensor comprises an optical fiber 100 having a reagent 120 (such as an antigen for example) coated onto its distal end. A reagent 122 (such as an antibody, for example), conjugated with an enzyme label 124, is sealed by a membrane 130 in a dialysis package. The reagent antibody 122 is complementary with reagent antigen layer 120. Therefore, the reagent antibody 122 always has a tendency to bond to the reagent antigen layer 120 before a sample antibody is detected. This structure is immersed into a sample solution 150 to determine whether the sample 150 includes an antibody 140 which is also complementary to reagent 120. As shown in FIG. 1d, if the sample solution 150 includes the antibody, it will tend to bond to reagent layer 120 at the distal end of the optical fiber 100, competing with the fluorescent-labeled reagent 122. The optical fiber 100 is then illuminated with a light source (not shown) at its proximal end. Any labeled reagent 122 remaining bonded to reagent layer 120 will become excited by the light and will return a fluorescent signal. In this case, the higher the concentration of antibody 140 in the sample solution 150, the more labeled reagent 122 will leave the coated reagent 120 at the end of the optical fiber 100, and hence, the lower the intensity of any returned fluorescent signal. Thus, the concentration of antibody 140 is inversely proportional to the returned light intensity.

The above mentioned fiber optic biosensors have a number of disadvantages. Regarding the sandwich type fiber optic biosensor, the optical fiber 100 must first be immersed in the sample solution 104, washed, and then be immersed in a solution 108 including labeled reagent 110. Thus, this sandwich type assay is heterogeneous, and two discrete reaction steps must be performed. Consequently, only an endpoint concentration can be determined. The rate at which the antibodies 106 are bonded with the reagent 102 cannot be determined in real time. Furthermore, the sandwich type fiber optic biosensor cannot be used for most in vivo testing because of the heterogeneous assay format being used, and because most labels (e.g., a fluorescent indicator) are potentially toxic. Moreover, most labels have poor stability in storage, particularly if exposed to light. Also, the optical intensity signal utilized in these methods is susceptible to environment and system induced noises, such as light source instability, temperature changes, and fiber-bend introduced light losses.

Regarding the displacement type fiber optic biosensor, the membrane 130 adds cost and size to the biosensor. Further, the displacement type fiber optic biosensor is not well suited for in vivo testing; again, due to its size and the potential toxicity of the labels used with the reagent.

An other type of optical biosensor is known as surface plasmon resonance (or "SPR") sensors. A known bulk optic SPR sensor, shown in FIG. 2a, includes a prism 202 having a very thin metal layer 204 which forms an interface with a bulk dielectric 208. An incident beam 206 of transverse magnetically polarized monochromatic light enters the prism 202 at a first face, is reflected by the metal layer 204, and exits a second face of the prism 202. The intensity of the reflected beam is later measured for various angles θ of the incident light beam 206. As shown in FIG. 2b, the intensity of the reflected beam drops at a particular angle of incidence $\theta_{sp}$, at which the energy of the incident light is coupled with surface plasmon (or "SP") waves which are excited at the metal-dielectric interface. If a film is deposited on the thin metal layer 204, the effective refractive index of the bulk dielectric material changes, especially at the vicinity of the metal layer 204. This effective refractive index depends on the refractive indices of the bulk dielectric material and the deposited film, and the thicknesses and density of the deposited film. Thus, if the thickness of the deposited film changes, the effective index of refraction also changes, and therefore the critical angle of incidence $\theta_{sp}$ changes. By determining the critical angle of incidence $\theta_{sp}$, the thickness and/or density of the deposited film can be derived.

In a fiber optic version of the SPR sensors, the signal is detected in a similar manner to the bulk optic versions. Instead of a monochromatic light source, a polychromatic light source with a range of wavelengths is employed for illumination. Here, the optical coupling efficiency varies with the changing wavelengths. At a certain wavelength, the intensity of the reflected light reaches a minimum value. Further, when the thickness and/or density of a deposited film changes, the wavelength at which the minimum reflection occurs also shifts from one value to another. Therefore, by tracing the shift of the wavelength at which the minimum reflection occurs, the thickness and/or density of the deposited film onto the cylindrical surface of the fiber can be determined.

The article, R. C. Jorgenson et al., "A Novel Surface Plasmon Resonance Based Fiber Optic Sensor Applied to Biochemical Sensing," *Fiber Optic Sensors in Medical Diagnostics*, SPIE Vol. 1886, pp. 35–48 (1993) (hereinafter referred to as "the Jorgenson article") discusses a SPR based fiber optic sensor for use as a dip-probe to quantify proteins in a solution. The probe discussed in this SPR article, shown in FIG. 2c, includes a multi-mode optical fiber 210 having a section of its cladding 212 removed and coated with a coupling metallic film 214, such as silver for example.

FIG. 2d illustrates the probe, similar to that of FIG. 2c, in a system. The system includes a light source 220, optically coupled via optical fiber 232 with a beam splitter 222. The light source 220 is polychromatic, which provides a range of wavelengths. An output of the beam splitter 222 is optically coupled, via connector 224, and optical fiber 238, with a mode scrambler 226. The mode scrambler 226 is optically coupled with the core and cladding 210/212 of the optical fiber of the probe which is immersed in a liquid sample 216.

A signal, reflected from a 3000 Angstrom silver mirror 218 at the distal tip of the fiber optic core 210 is provided to a spectrograph 230 via mode scrambler 226, optical fiber 238, connector 224, beam splitter 222, and optical fiber 236. The spectrograph 230 is used to measure intensity as a function of wavelength. Based on this data, the thickness of a film which develops on the 550 Angstrom silver or gold plating 214 can be determined.

Although the SPR probe discussed in the Jorgenson article is advantageous in that it does not require labels and because measurements can be continuously determined, it suffers from a number of disadvantages. Specifically, the SPR probe discussed in the Jorgenson article requires the use of thick multi-mode optical fiber rather than thin, single-mode, optical fiber. More importantly, in producing the SPR probe, a thin, highly reflective, metal layer must be deposited onto the optical fiber thereby increasing material and manufacturing costs. Lastly, the sensing section of the SPR probe is a relatively long cylindrical surface. This relatively large sensing area requires a relatively large amount of reagent and requires a relatively large test sample, thereby precluding most in vivo testing applications.

Yet another type of biosensor is known as grating biosensors. An example of a grating biosensor is discussed in the article, W. Lukosz et al., "Output Grating Couplers on Planar Optical Waveguides as Direct Immunosensors," *Biosensors and Bioelectronics*, Vol. 6, pp. 227–232 (1991) (hereinafter referred to as "the Lukosz article") and shown in FIG. 3. As shown in FIG. 3, an incident beam of laser light 302 is optically coupled with the end of a planar waveguide 304. The planar waveguide 304 includes a very thin film 306 of high refractive index on a glass substrate 308. A section of the very thin film 306 is provided with surface relief grating 310. The surface relief grating 310 couples an excited guided mode of the laser light 302 out of the planar waveguide 304 at an angle α to the normal of the planar waveguide 304. The angle α is related to the effective refractive index of the guided mode.

The surface relief grating 310 may be provided with a layer of reagent. A liquid test sample 314 may be provided in a basin 312 surrounding the surface relief grating 310. If contents of the liquid test sample 314 bond with the reagent layer, the effective refractive index will change, thereby changing the diffraction angle α.

The outcoupled beam is focused, by lens 316, onto a one-dimensional position sensitive photodetector (or "PSD") 318. The output of the PSD 318 is sampled by an analog-to-digital converter 320 and provided to a personal computer 322 for analysis. A change in the angle α of the outcoupled beam, which is caused by a change in the effective refractive index, manifests itself as a translation Δu on the PSD 318. This translation is related to the thickness of a film consisting of the reagent and any bonded elements forming a film on the surface relief grating 314.

Grating biosensors have a number of drawbacks. First, as reported in the Lukosz article, when $SiO_2$—$TiO_2$ waveguides contact aqueous buffer solutions, the effective indices of refraction slowly increase. This is known as the "drift effect". With test samples having low concentrations of elements to be detected, the slow increase in effective indices of refraction cannot be differentiated from the drift effect with certainty. Second, the grating biosensor discussed in the Lukosz article cannot perform remote sensing functions. Moreover, due to its relatively large size, it cannot be used for many in vivo sensing applications. This relatively large size also makes conducting multiple tests of a single sample difficult. Furthermore, the sensing section (i.e., the surface relief grating of the waveguide) is relatively long. Thus, a large quantity of sample solution is required. Finally, fabricating planar waveguides with built-in gratings involves a complex and costly process, particularly onto a microvessel.

Still another type of biosensor is known as a microcuvette-based Fabry-Perot (or "FP") interferometer biosensor. An example of this biosensor is discussed in the paper, Brecht et al., "Direct Monitoring of Antigen- Antibody Interactions by Spectral Interferometry," *Sensors and Actuators*, Vol. 6, pp. 96–100 (1992) (hereinafter referred to as "the Brecht article"). As shown in FIG. 5, in the microcuvette-based FP interferometer discussed in the Brecht article, a glass or quartz slide forms a substrate 514 which is provided with a film 502 of polystyrene, polysilozane, or silicon dioxide.

As shown in FIG. 6, the substrate 514 and film 502 are attached to the bottom of a flow cell 602 with a silicon seal. A bifurcated multistrand quartz optical fiber 604 is optically coupled normal to the substrate 514. An end of a first branch 606 of the optical fiber 604 is coupled with a spectrometer 610 (such as a diode array photometer), while an end of a second branch 608 of the optical fiber 604 is coupled with a light source 612 (such as a xenon light source or a 20 Watt halogen light source).

Next, a solution containing a predetermined concentration of a reagent 504, such as an immunoglobin antigen, is passed through the flow cell 602 for a predetermined period of time whereby an layer of antigens 504 is provided on the film 502. Washing the structure is used to halt an increasing thickness of the antigen layer 504. Ovalbumin (i.e., egg white protein) is then used for blocking. Another washing step is then performed.

Finally, a sample solution is passed through the flow cell 602 for a predetermined period of time. If the sample solution includes antibodies 506 complementary to the antigens 504, they will bond to the structure thereby further increasing the thickness of the structure. Since the protein molecules are often smaller than the wavelength of the light supplied by the light source 612, an increase in the coverage of a monomolecular protein layer can be treated as an increase in the thickness of a homogeneous film.

The spectrometer 610 is used to determine the spectrum and intensity of the reflected light waves at different times. For example, FIG. 4 shows an output "A" of the spectrometer 610 at a first time and an output "B" of the spectrometer 610 at a subsequent time when the thickness of the film has increased. The thickness Δ of the layer can be determined based on Fresnel's law. That is, the intensity I of interfering light reflected at the interfaces of a thin film can be represented by:

$$I = I_1 + I_2 + 2\sqrt{I_1 I_2} \cos\left(\frac{2\pi\Delta}{\lambda}\right)$$

where
$I_1$ and $I_2$ denote the intensity of reflected partial beams from the film interfaces,
Δ denotes the effective optical path difference between the two partial beams, and
λ denotes the wavelength of incident light.
Assuming that the intensities of the reflected light are equal, the following relationship results:

$$I = 2I_R\left(1 + \cos\left(\frac{2\Pi\Delta}{\lambda}\right)\right)$$

Thus, the effective optical path difference Δ (and hence thickness of the film) can be determined based on the intensity of the reflected light and the wavelength of the light.

Although the microcuvette-based Fabry-Perot interferometer biosensor discussed above is advantageous in that the reagent need not be labeled and because analysis is not limited to end-point data, it does suffer from several drawbacks. First, the area of the microcuvette (i.e., the slide) is relatively large. Consequently, thick multistrand optical fiber cable must be used rather than a thin single strand optical fiber. Also, the relatively large area of the microcuvette necessitates large sample volumes or high sample concentrations. Lastly, the relatively large area of the microcuvette precludes its use for in vivo testing. Further, as shown in FIG. 5, redundant reflections from the substrate interfaces contribute fluctuating noises to the detector. Furthermore, the microcuvette slides are relatively expensive due to their size, the materials used, and procedures required to form them. Thus, although microcuvette-based Fabry-Perot interferometer biosensors may be practical for research purposes, they are not feasible for widespread commercial testing, nor are they feasible as a disposable sensor. Lastly, as shown in FIG. 6, in the microcuvette-based Fabry-Perot interferometer biosensor, the substrate with film 500 is arranged in the bottom of a flow cell 602. This traditional bottom sensing arrangement potentially increases the likelihood of non-specific binding. That is, there is an increased likelihood that the reagent (e.g., an antigen) will bond with a non-complimentary antibody.

In view of the problems associated with the above described biosensors, an improved biosensor is needed. The improved biosensor should:

i) have a simple structure to permit a low cost, preferably disposable, probe;

ii) permit multiple assays to be performed simultaneously;

iii) work without unstable and potentially toxic labels or indicators;

iv) be feasible for in vivo testing;

v) permit continuous data acquisition for monitoring rate of reaction, as well as end-point data acquisition;

vi) permit real time data analysis;

vii) be electrically isolated from a patient for safe in vivo testing;

viii) permit real time calibration of the probe;

ix) have a relatively small probe;

x) prevent non-specific bondings;

xi) be highly sensitive; and xii) have a large linear range.

SUMMARY OF THE INVENTION

My invention provides an improved biosensing method and biosensor which overcomes the aforementioned problems of known biosensors. Specifically, my biosensing method permits the concentration of a substance in a sample solution to be determined using a fiber optic probe having a reagent at its distal end to which the substance bonds. The method of my invention includes steps of (i) immersing the distal end of the fiber optic probe into the sample solution, (ii) optically coupling a light source with the proximal end of the fiber optic probe, (iii) detecting at least a first light beam reflected from an interface between the distal end surface of the fiber optic section and the reagent layer, and a second light beam reflected from an interface between the reagent layer and the sample solution, reflected from the distal end of the fiber optic probe, (iv) detecting an interference pattern (e.g., a diffraction pattern) formed by the first and second light beams at a first time, (v) detecting an interference pattern formed by the first and second light beams at a second time, and (vi) determining whether the substance is present in the sample solution based on whether a shift occurs in the interference patterns. The concentration of the substance may be determined based on a shift in the interference patterns and based on a differential between the first and second times.

In a preferred embodiment of my method, each step of detecting includes sub-steps of (i) dispersing an interference beam, formed by the first and second light beams, onto a spectrometer, (ii) determining a periodic function based on the spectral dispersion pattern (e.g., a diffraction pattern), and (iii) determining a phase of the periodic function.

In an alternative methodology of my invention, the frequency of the light source optically coupled with the proximal end of the fiber optic probe is modulated and the step of determining whether the substance is present in the sample solution is synchronized with the frequency of the light source.

My invention also provides a probe for detecting, in one step, the concentration of a substance in a sample solution. The probe of my invention includes a fiber optic section having a proximal end tip and a distal end tip and a reagent layer disposed on the distal end tip. The reagent layer reacts (or bonds) with the substance (analyte) being detected. The fiber optic section has a first index of refraction and the reagent layer has a second index of refraction. When any of the substance bonds to the reagent layer, a resulting layer including the reagent layer and the substance is formed. The resulting layer can be treated as having a homogeneous index of refraction.

The fiber optic section may be a single mode or a multi-mode optical fiber, having a diameter of at least 3 $\mu$m and preferably, of approximately 100 $\mu$m.

The reagent may be an antibody, an antigen, a natural or synthetic protein, a DNA segment, or a chemical. The substance (analyte) to be detected may be an antibody, an antigen, a natural or synthetic protein, a DNA segment, or a chemical.

My invention further provides a system for detecting the concentration of a substance in a sample solution. My system has a light source for providing a light beam, a fiber optic probe, a detector, a fiber optic coupler, a fiber optic connector, and a processor. The fiber optic coupler includes a first fiber optic section having a proximal end for receiving an incident light beam, a second fiber optic section having a proximal end for delivering the reflected interference light beam to the detector, and a third fiber optic section having a distal end for connecting to the fiber optic probe. The fiber optic probe includes a proximal end for connecting to the fiber optic coupler, and a distal end tip with a reagent layer disposed thereon. The fiber optic probe produces at least a first reflected beam and a second reflected beam from the incident light beam. The detector detects an interference pattern formed by the first and second reflected beams. The coupler optically couples the light source with the fiber optic probe and optically couples the fiber optic probe with the detector. The processor determines a phase associated with an interference pattern detected by the detector at a first time, determines a phase associated with an interference pattern detected by the detector at a second time, and determines the concentration of the substance based on a shift in the phases associated with the interference patterns detected by the detector at the first and second times.

In a preferred embodiment of the system of my invention, the detector is a spectrometer, such as a one-dimensional (e.g., 1×1024) charge coupled device.

In a preferred embodiment of the system of my invention, the processor includes a periodic signal generator, a phase tracker, and a computer. The periodic signal generator generates a first periodic signal based on the interference pattern detected by the detector at the first time and a second periodic signal based on the interference pattern detected by the detector at the second time. The phase tracker determines a phase of the first periodic signal and a phase of the second periodic signal. The computer determines a phase difference between the phases of the first and second periodic signals and determines the concentration of the substance in the sample solution based on the phase difference.

In a preferred embodiment of the system of my invention, the coupler is a "Y"-type coupler and the light source may be a broadband light source or a super radiant diode.

In an alternative embodiment of a system of my invention, the system further includes a frequency modulator, coupled with the light source, for modulating the frequency of the light beam provided by the light source. In this embodiment, the processor is synchronized with the frequency modulator.

In yet another alternative embodiment of the system of my invention, the system further includes a second fiber optic probe, an optical multiplexer and an optical demultiplexer. The second fiber optic probe is used for determining the concentration of a second substance in the sample solution. The optical multiplexer is coupled between the light source and each of the first fiber optic probe and the second fiber optic probe, and optically couples the light source with one of the fiber optic probes in a time division manner. The optical demultiplexer is coupled between each of the fiber optic probes and the detector. The optical multiplexer and the optical demultiplexer are synchronized with each other.

BRIEF DESCRIPTION OF THE DRAWINGS

FIGS. 2a through 2d depict conventional (i.e. prior art) devices.

DETAILED DESCRIPTION

In the following, the meaning of the "concentration" of a substance in a sample solution shall include whether or not the sample solution contains any of the substance. That is, if the sample solution does not include any of the substance, the "concentration" of the substance in the solution will be zero (0). Also, in the following, the term "immobilized" shall be interpreted to include, but not be limited to, coated or disposed.

Figure 1A:
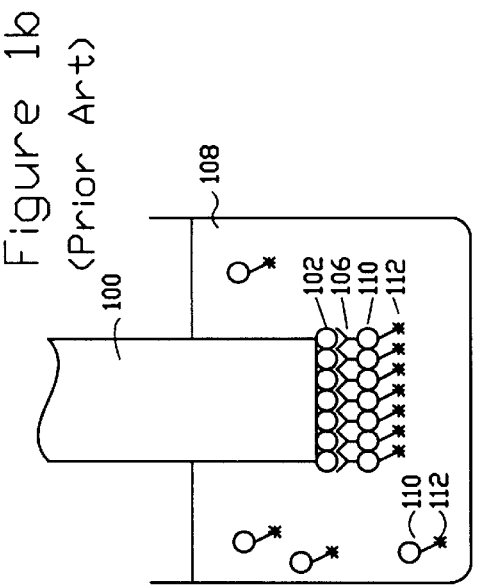
FIGS. 1a, 1b, 1c and 1d illustrate conventional (i.e. prior art) sandwich type and displacement or competitive type fiber optic fluorescent biosensors.
Figure 1C:
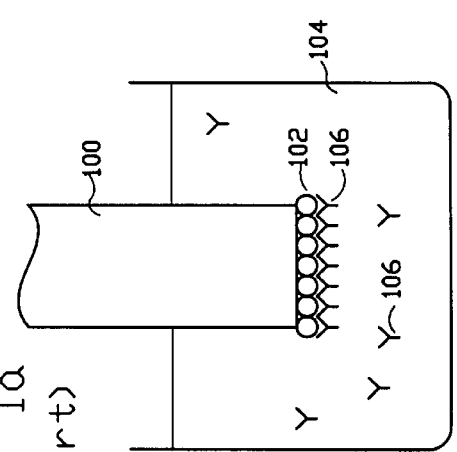
Figure 1B:
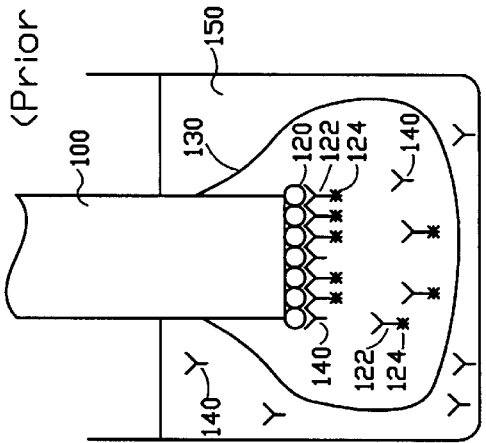
Figure 1D:
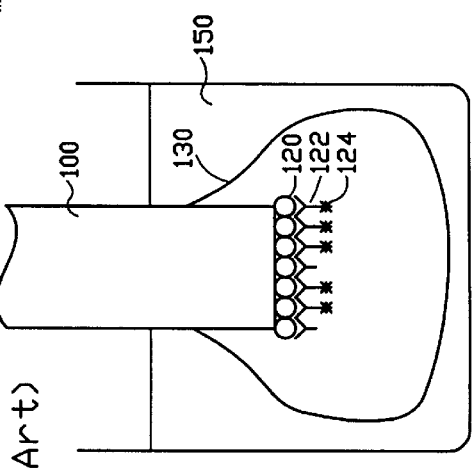
Figure 2B:
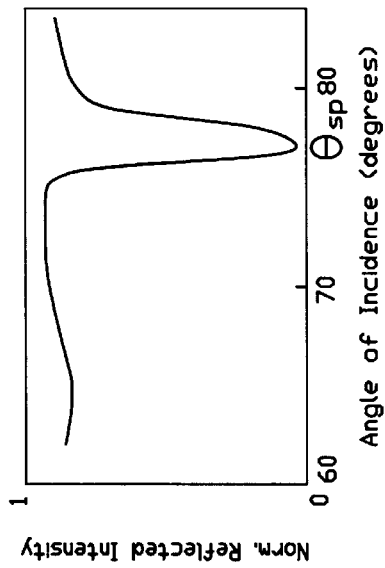
FIG. 2b is a plot of reflection intensity versus angle of incidence in a bulk-optic surface plasmon resonance sensor.
Figure 2A:
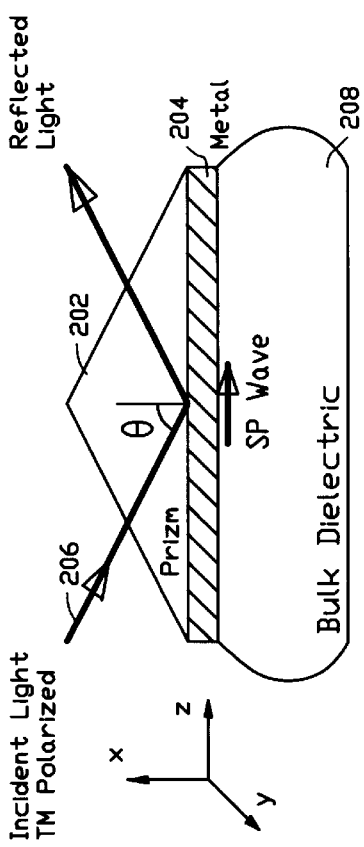
FIG. 2a illustrates cross-sectional side view of a bulk-optic surface plasmon resonance sensor.
Figure 2C:
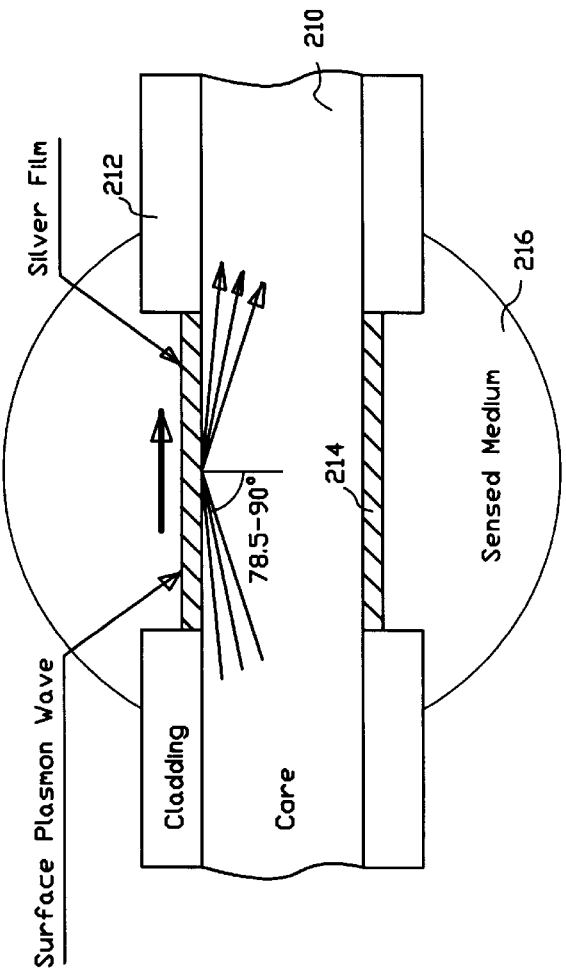
FIG. 2c is a cross-sectional side view of a fiber optic surface plasmon resonance sensor probe.
Figure 2D:
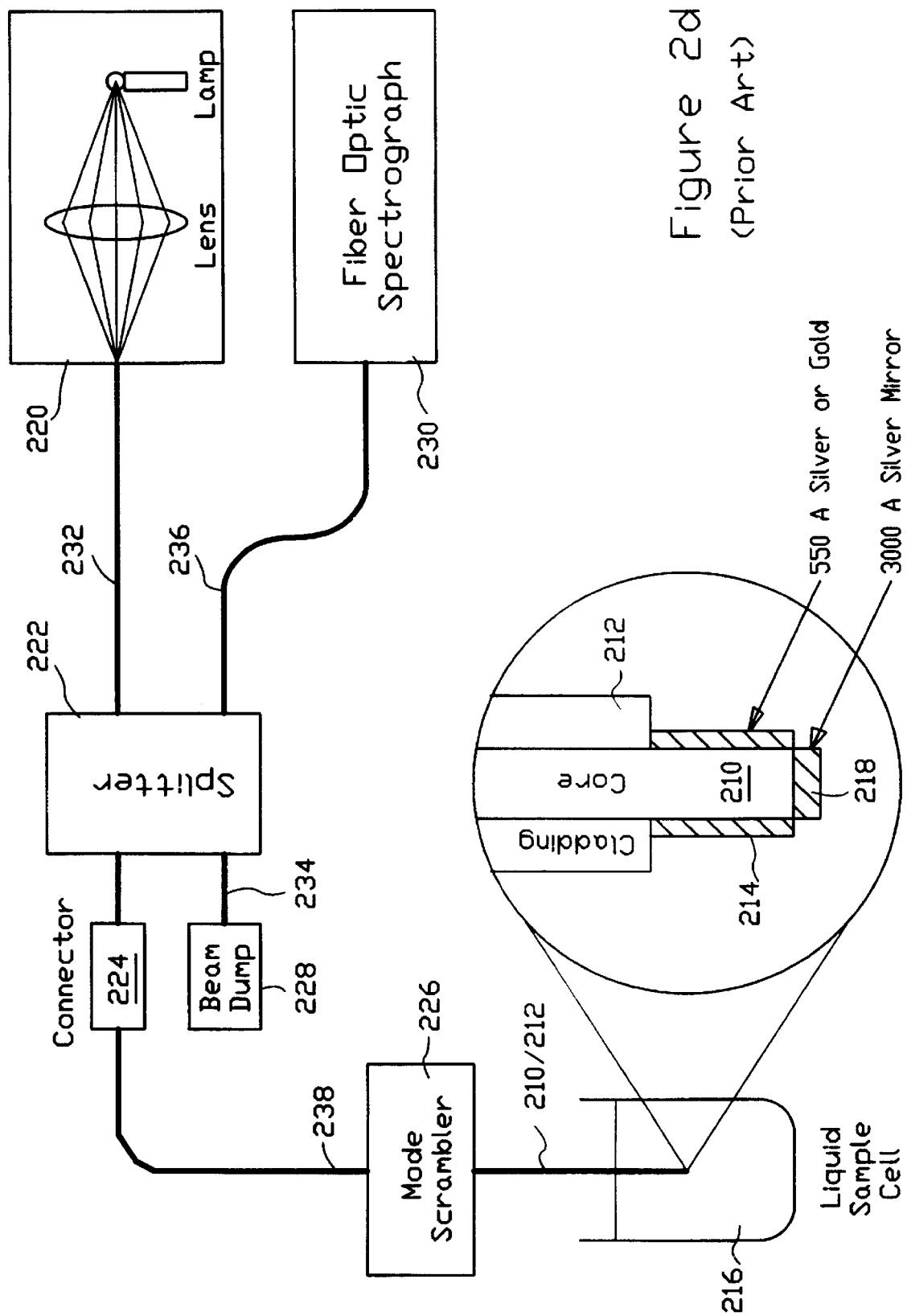
FIG. 2d is a block schematic of a system using a fiber optic surface plasmon resonance bioprobe.
Figure 3:
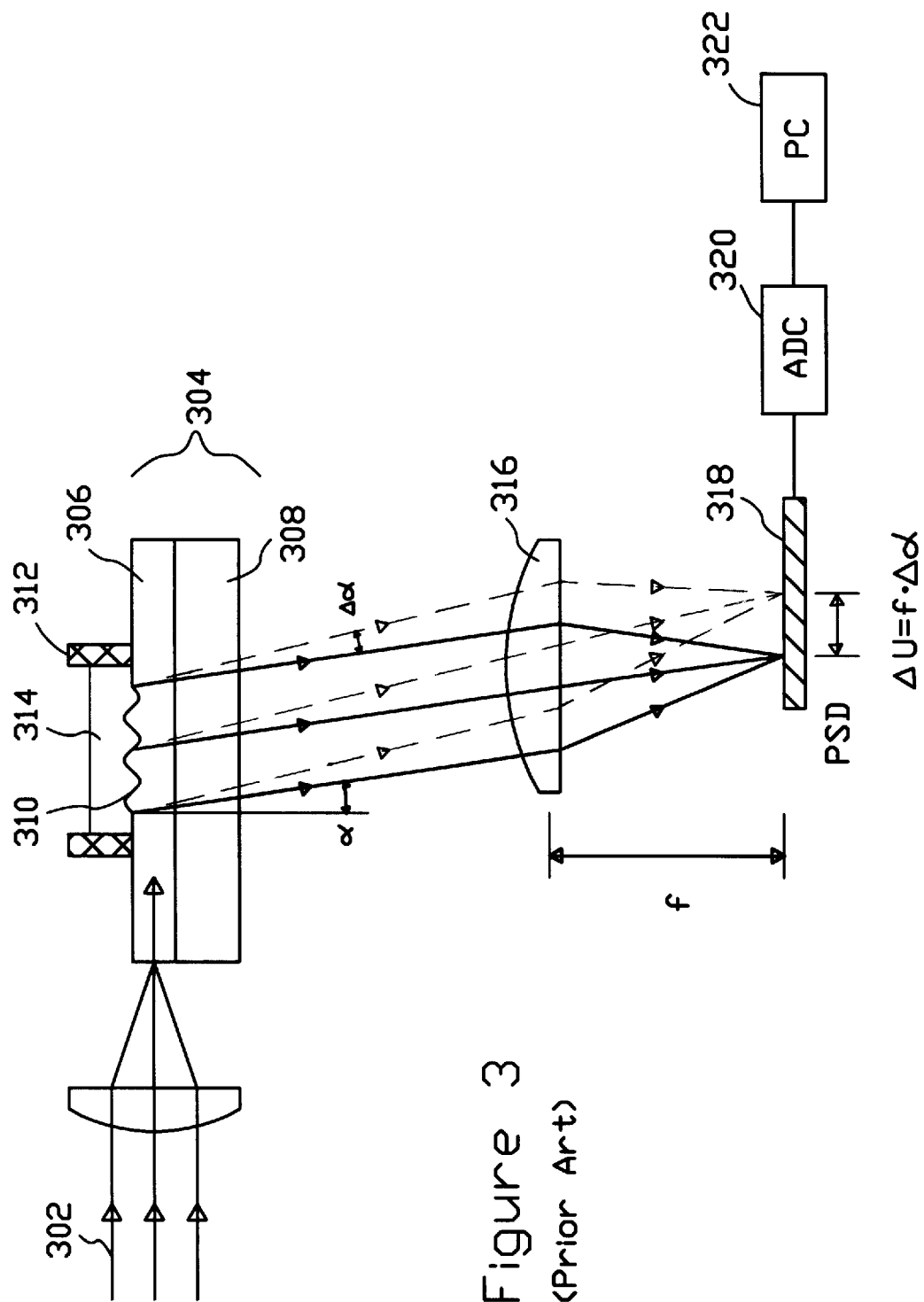
FIG. 3 is schematic which illustrates the operation of a conventional (i.e. prior art) output grating bioprobe.
Figure 4:
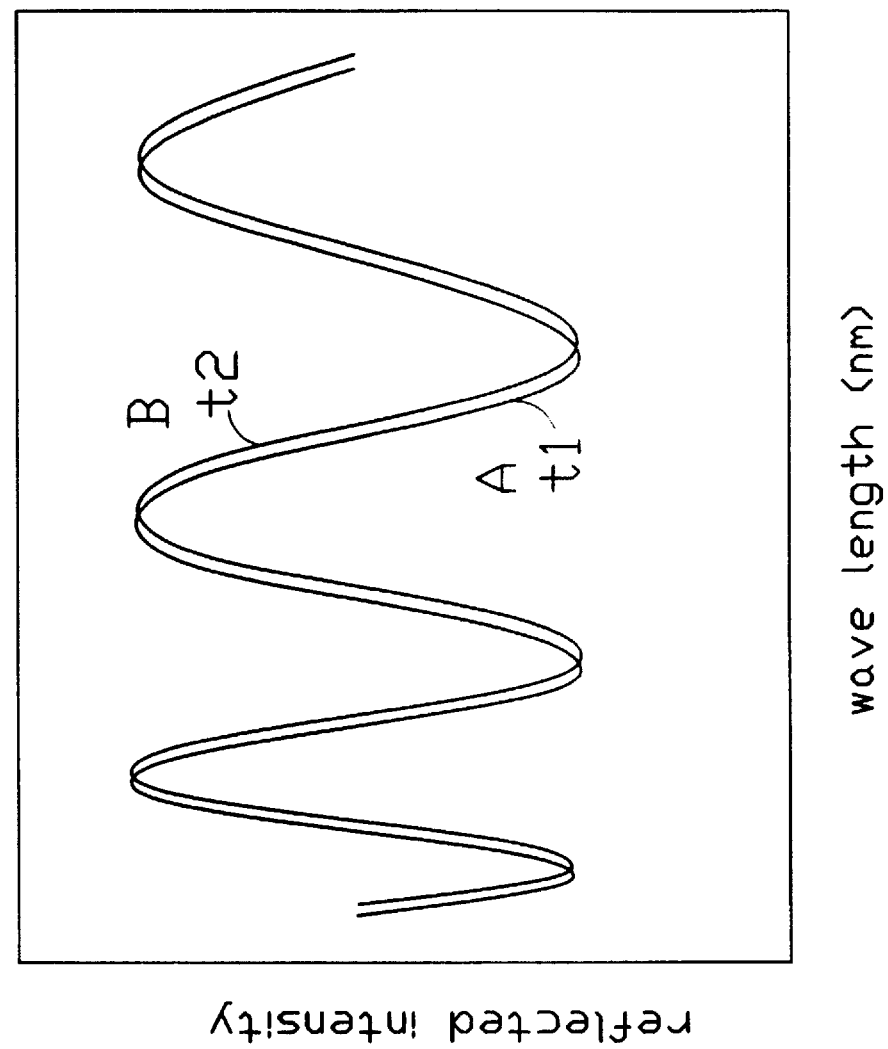
FIG. 4 is a plot of reflected intensity versus wavelength in the conventional (i.e. prior art) microcuvette-based Fabry-Perot interferometer biosensor at a first time $t_1$ and at a subsequent time $t_2$.
Figure 5:
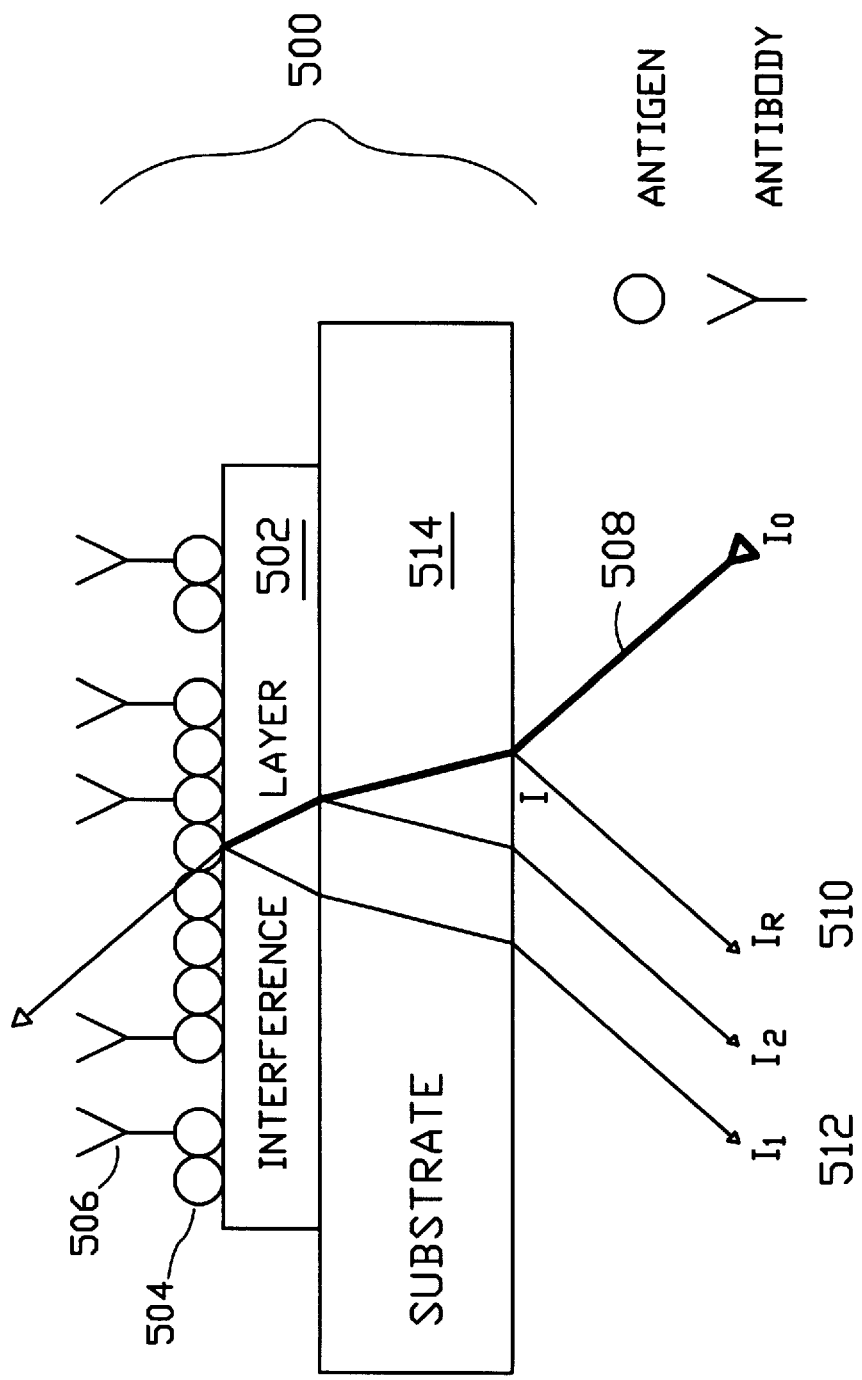
FIG. 5 is a cross sectional view of a slide used in the conventional (i.e. prior art) microcuvette-based Fabre-Perot interferometer biosensor.
Figure 6:
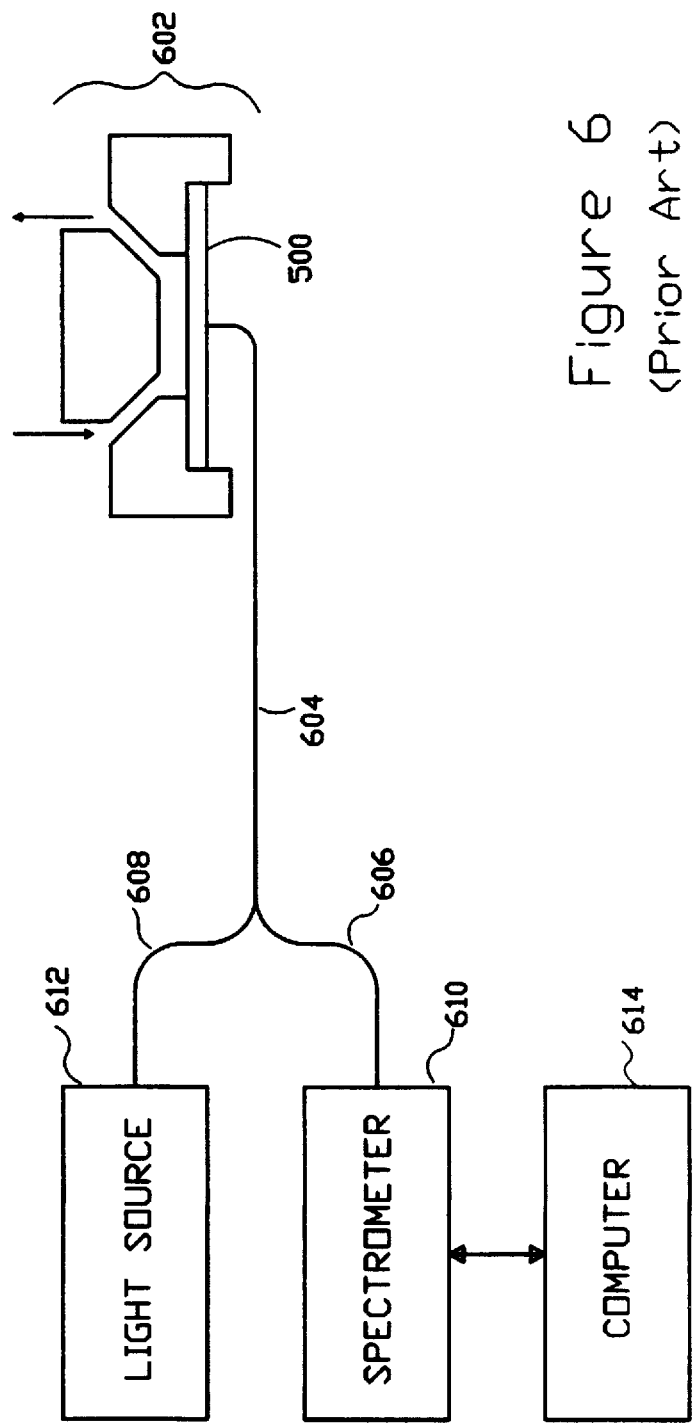
FIG. 6 is a schematic which illustrates the system used for the conventional (i.e. prior art) microcuvette-based Fabre-Perot interferometer biosensor.
Figure 7B:
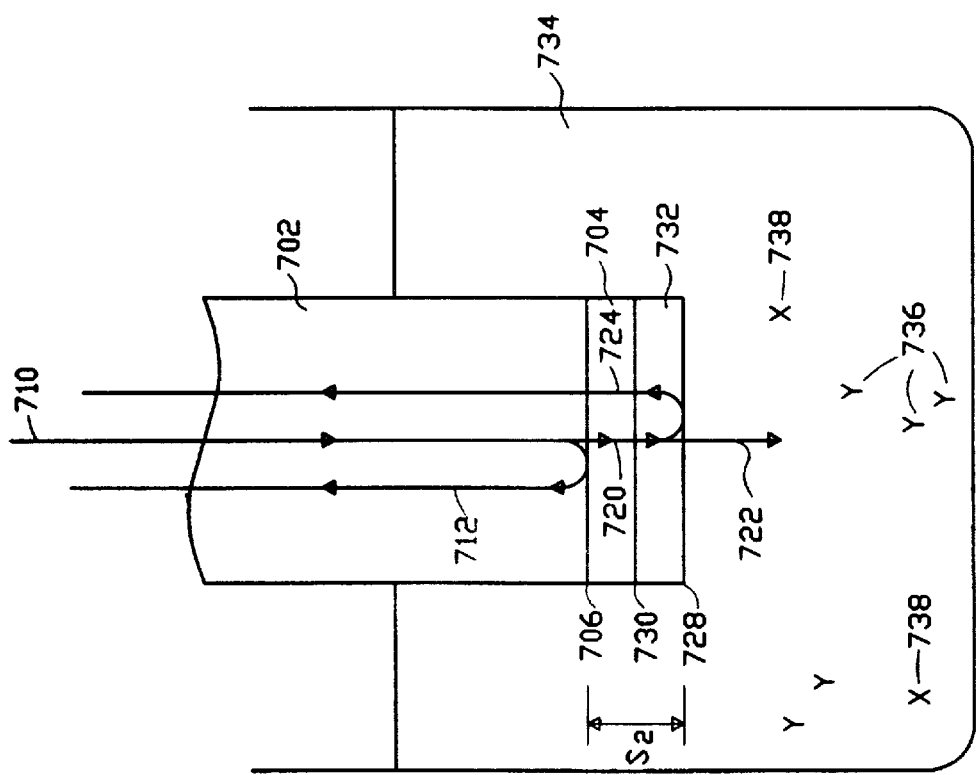
FIGS. 7a and 7b illustrate the operation of the bioprobe used with the biosensor of my invention.
Figure 7A:
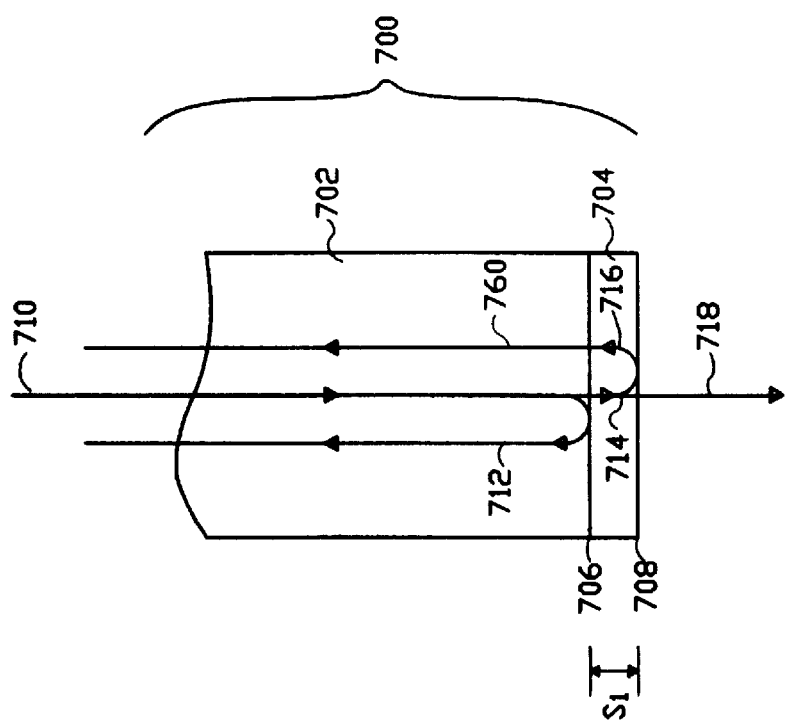

FIGS. 7a and 7b illustrate the principle of my invention. As shown in FIG. 7a, a biosensor probe 700 includes an optical fiber 702 and a reagent 704 which is bonded to a distal tip of the optical fiber 702. The reagent 704 may be an antigen, such as an immunoglobin antigen. The reagent may also be a particular antibody, chemical, DNA segment, enzyme or protein. The reagent 704 may be bonded to the tip of the optical fiber 702 by coating the tip with a solution having a predetermined concentration of the reagent for a predetermined time period until a layer of the reagent 704 is formed on the tip of the optical fiber 702. The resulting structure may then be washed and blocked. Other methods of forming the reagent layer 704 on the tip of the optical fiber 702 will be apparent to those skilled in the art. Such methods may be dictated by the particular reagent being applied.

An incident light beam 710 is sent through the optical fiber 702 toward its distal end. At the interface 706 defined between the optical fiber 702, which has a first index of refraction, and the reagent 704, which has a second index of refraction, a first portion 712 of the incident light beam 710 will be reflected, while a second portion 714 of the incident light beam 710 will continue through the reagent 704. At an interface 708 defined at the exposed surface of the reagent 704, of the second portion 714 of the incident beam 710, a first portion 716 will be reflected, while a second portion 718 will pass into the adjacent medium. Of the first portion 716 of the second portion 714 of the incident beam 710, a first portion 760 will be transmitted back through the optical fiber 702, while a second portion (not shown) will be reflected at the interface 706 back into the reagent layer 704.

As described in more detail below, at a proximal end of the optical fiber 702, the reflected beams 712 and 760 are detected and analyzed. At any given point along the optical fiber 702, including its proximal end, the reflected beams 712 and 760 will exhibit a phase difference. Based on this phase difference, the thickness $S_1$ of the reagent layer 704 can be determined.

As shown in FIG. 7b, the probe 700 is immersed in a sample solution 734 to determine whether any antibodies 736, which are complementary with the reagent antigen 704, are present in the sample solution 734 and to determine the concentration of any such complementary antibodies 736 in the sample solution 734. Since complementary antibodies 736 are characterized by a specific reactivity with the antigen reagent 704, these antibodies 736 will bond to the antigen reagent layer 704, thereby forming an antibody layer 732 over a period of time. The thickness $S_2$ of the layer will be a function of the time of immersion of the probe 700 in the sample fluid 734, as well as the concentration of the antibodies 736 in the sample fluid 734. Other, non-complementary antibodies 738 will not bond with the antigen reagent layer 704. The "overlook" arrangement of the probe 700 with respect to the sample fluid 734 diminishes the likelihood of non-specific bonding. That is, this arrangement diminishes the likelihood of bonding between non-complementary antibodies 738 and the antigen reagent 704.

Typically, the molecules of the proteins (i.e., antigens and antibodies) being analyzed will be small relative to the wavelength of the incident light beam 710. Therefore, from an optical perspective, the reagent layer 704 and the antibody layer 732 can be treated as a single layer. That is, the interface 730 between the reagent layer 704 and the antibody layer 732 is usually insignificant, optically speaking. Thus, the combined reagent layer 704 and antibody layer 732 of FIG. 7b will behave similarly, optically speaking, to the reagent layer 704 of FIG. 7a. However, the total thickness $S_2$ of this combined layer will be greater than the thickness $S_1$ of the reagent layer 704 alone. Thus, similar to the probe 700 of FIG. 7a, when an incident beam 710 is directed towards the distal tip of the optical fiber 702, at the interface 706 between the optical fiber 702 and the combined layer, a first portion 712 of the incident beam 710 is reflected, while a second portion 720 of the incident beam 710 continues through the combined layer. At a second interface 728 between the combined layer and the sample solution 734, a first portion 724 of the second portion 720 of the incident beam 710 is reflected, while a second portion 722 of the second portion 720 of the incident beam 710 continues through the sample solution 734. Of the first portion 724 of the second portion 720 of the incident beam 710, a first portion 726 continues back through the optical fiber 702, while a second portion (not shown) is reflected back into the combined layer at the interface 706.

At a proximal end of the optical fiber 702, the reflected beams 712 and 726 are detected and analyzed. At any given point along the optical fiber 702, including its proximal end, the reflected beams 712 and 726 will exhibit a phase difference. Based on this phase difference, the thickness $S_2$ of the combined layer can be determined.

By determining the difference between the thickness $S_2$ of the combined layer and the thickness $S_1$ of the reagent layer 704, the thickness of the antibody layer 732 can be determined. Based on this thickness, the presence of complementary antibodies 736 in the sample solution may be determined. Further, the thickness $S_2$ of the combined layer can be determined (or "sampled") at discrete points in time. In this way, the rate of increase of the difference between the thickness $S_2$ of the combined layer and the thickness $S_1$ of the reagent layer 704 (i.e., the rate of increase in thickness of the antibody layer 732) can be determined. Based on this rate, the concentration of complementary antibodies 736 in the sample solution 734 can be determined within a very short incubation period.

Figure 8:
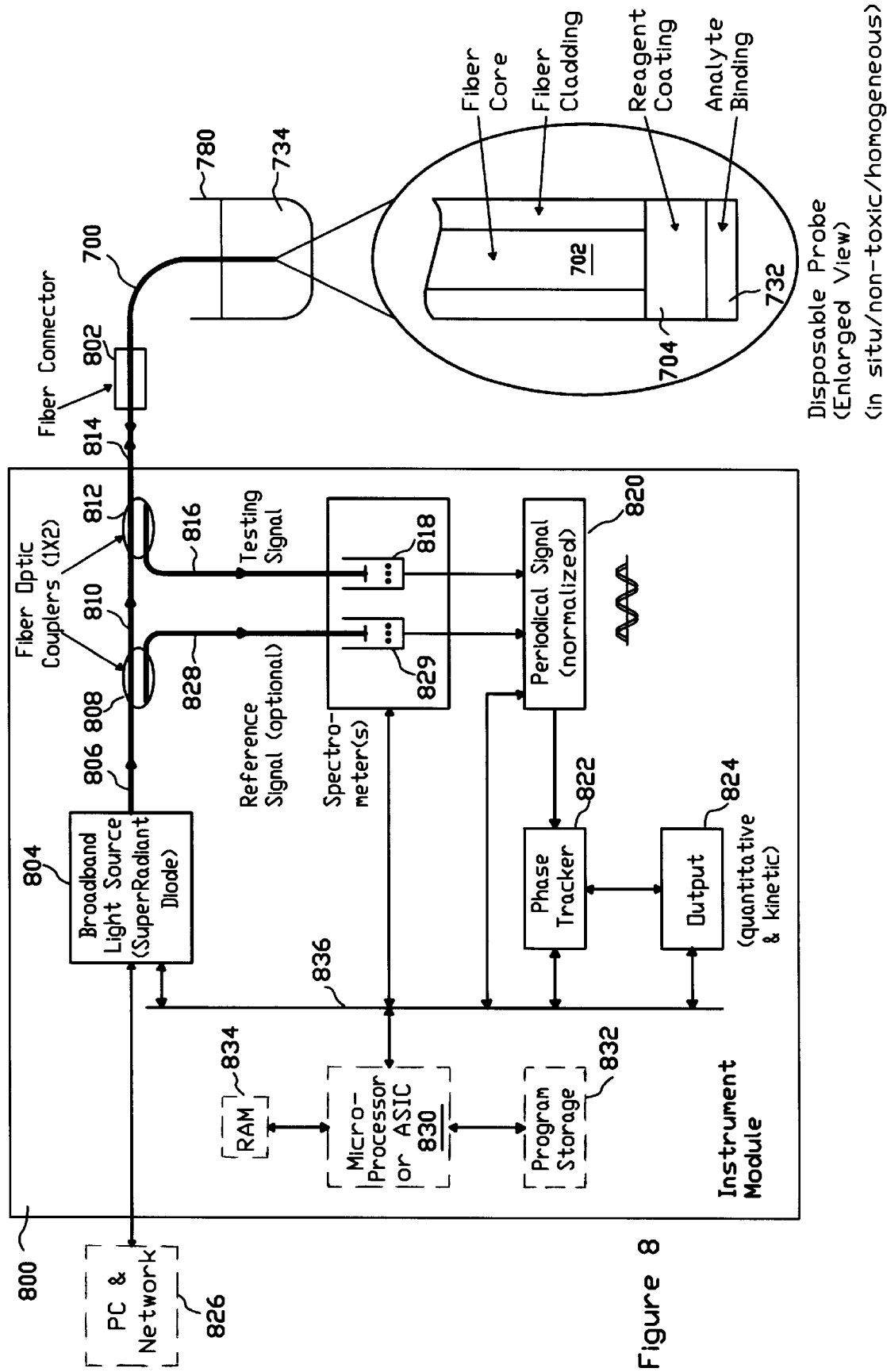
FIG. 8 is a schematic of a first embodiment of the biosensor of my invention.

FIG. 8 is a schematic diagram which illustrates a first embodiment of my improved biosensor using the above described bioprobe 700. To reiterate, the bioprobe 700, including an optical fiber 702 and reagent 704 bonded to the distal tip of the optical fiber 702, is immersed in a sample solution 734. As shown in the blown up portion, a fiber cladding surrounds a longitudinal surface of the fiber core adjacent to a distal end of the fiber core. More specifically, the fiber cladding surrounds the fiber core from a proximal end tip to a distal end tip. The sample solution is contained within a test tube 780, for example. The bioprobe 700 is optically coupled, via connector 802, with a biosensor optical analyzer 800.

The biosensor optical analyzer 800 includes a light source 804, a spectrometer 818, a periodic signal generator 820, a phase tracker 822 and an output device 824. The biosensor optical analyzer 800 can be operated in a number of ways, for example: (i) via commands from an external computer or computer network 826; (ii) via commands from a dedicated microprocessor 830 which executes instructions from a program storage 832 and includes a RAM 834; or via commands issued from an application specific integrated circuit (or "ASIC") 830.

In this first embodiment, the light source 804 is a broadband light source, such as a super radiant diode for example. The light source 804 may be a tungsten halogen source manufactured by Ocean Optics (part no. LS1) for example. The light source 804 provides a light beam to an optical waveguide 806, such as an optical fiber for example. An optional optical coupler 808 may be used to optically couple the optical waveguide 806 with a further optical waveguide 828 which leads to an optional spectrometer 829. The optional spectrometer 829 preferably includes a one-dimensional (i.e., linear) charge coupled device (or "CCD"), such as a 1×1024 CCD, and is electrically coupled with a periodic signal generator 820. The optional spectrometer 829 may be a 600 to 700 nm spectrometer manufactured by Ocean Optics (part no. SD1000).

The optical coupler 808 also optically couples the optical waveguide 806 with another optical waveguide 810. An optical coupler 812 optically couples the optical waveguide 810 with a further optical waveguide 814. The optical waveguide 814 is optically coupled with the bioprobe 700, via the coupler 802.

The optical coupler 812 also optically couples the optical waveguide 814 with yet another optical waveguide 816. The optical waveguide 816 is optically coupled with a spectrometer 818. Like the optional spectrometer 829, the spectrometer 818 is preferably a one-dimensional CCD, such as a 1×1024 CCD, and is electrically coupled with the periodic signal generator 820.

Light emitted by the light source 804 is received by the bioprobe 700, via optical waveguide 806, optical coupler 808, optical waveguide 810, optical couple 812, optical waveguide 814, and optical coupler 802. As discussed above with reference to FIG. 7b, two reflected light beams 712 and 726 are sent back through the bioprobe 700. These reflected light beams 712 and 726 are received by the spectrometer 818 via connector 802, optical waveguide 814, optical coupler 812, and optical waveguide 816. As described above, these reflected light beams 712 and 726 are slightly out-of-phase due to the thickness $S_2$ of the combined layer. Thus, in accordance with Fresnel's law, these reflected light beams 712 and 726 form a diffraction pattern on the spectrometer 818. The diffraction pattern shifts as the thickness $S_2$ of the combined layer increases.

As the elements of the CCD in the spectrometer 818 are clocked out, a periodic (e.g., sinusoidal) wave is generated by the periodic signal interpreter/generator 820. The phase of the periodic (e.g., sinusoidal) wave, which is based on the diffraction pattern, is determined by the phase tracker 822. By comparing the phases of sinusoidal waves, which are based on diffraction patterns, sampled at the spectrometer at different times, the rate of increase of the thickness $S_2$ of the combined layer can be determined. This determination can be performed after data acquisition or, in real time during data acquisition.

Figures 9A, 9B:
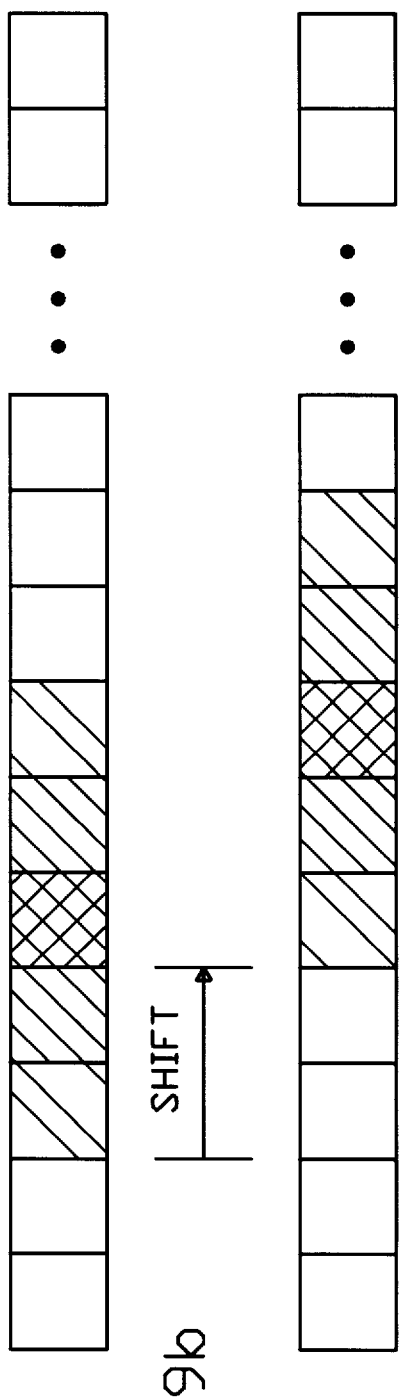
FIGS. 9a and 9b illustrate a shifted spectral dispersion pattern received by a one-dimensional charge coupled device of a spectrometer used in my biosensor.

Referring back to FIG. 7a, before the bioprobe 700 is immersed into the sample solution 734, the reflected beams 712 and 760 also form a diffraction pattern on the spectrometer 818 based on the thickness $S_1$ of the reagent 704. FIG. 9a shows a portion of that diffraction pattern (at a time before immersion of the bioprobe 700) shown on a portion of the one-dimensional CCD of the spectrometer 820. FIG. 9b shows a portion of a diffraction pattern (at a time after immersion of the bioprobe 700) shown on the portion of the one dimensional CCD of the spectrometer 820. As a comparison of FIGS. 9a and 9b shows, the diffraction pattern has shifted. Based on the amount of shift, whether or not antibodies 736, which are complementary with the antigen reagent 704, are present in the sample solution 734 can be determined. By sampling the one-dimensional CCD of the spectrometer at various times after immersion of the bioprobe 700, the rate of change of the shift, and thus, the concentration of any complementary antibodies 736 in the sample solution 734, can be derived.

In the first embodiment of my invention described with reference to FIG. 8, the optical waveguides 806, 810, 814, 816, and 828 are preferably single mode optical fiber, such as communications grade optical fiber for example. For example, 630 nm single mode fiber sold by Spectran or Corning may be used. However, multi-mode optical fiber may be used instead. For example, graded index fiber sold by Spectran or Corning may be used. The optical fiber is preferably at least 3 μm in diameter, and more preferably 100 μm in diameter.

The light coupler 808 and 812 are preferably "Y" (or two-by-one) optical couplers. For example, two-by-one optical couplings manufactured by E-TEK (part no. MMFCD150AH612) may be used. Alternatively, two-by-two optical couplers may also be used. If, however, two-by-two optical couplers are used, index matching gel should be applied to open ends to eliminate reflection noise. The fiber connector 802 may be part no. BFA-MM manufactured by MetroTek.

The optional spectrometer 829, which is optically coupled with the light source 804, is needed only if the frequency spectrum of the laser diode of the light source 804 is unstable. Specifically, the optional spectrometer 829 is used to distinguish drift in the frequency of the light source from a phase shift due to a thickening layer at the distal tip of the bioprobe 700. If, however, the frequency spectrum of the laser diode of the light source 804 is very stable, the optional spectrometer 829, as well as the optical coupler 808 and the optical waveguide 828, are not needed.

Figure 10:
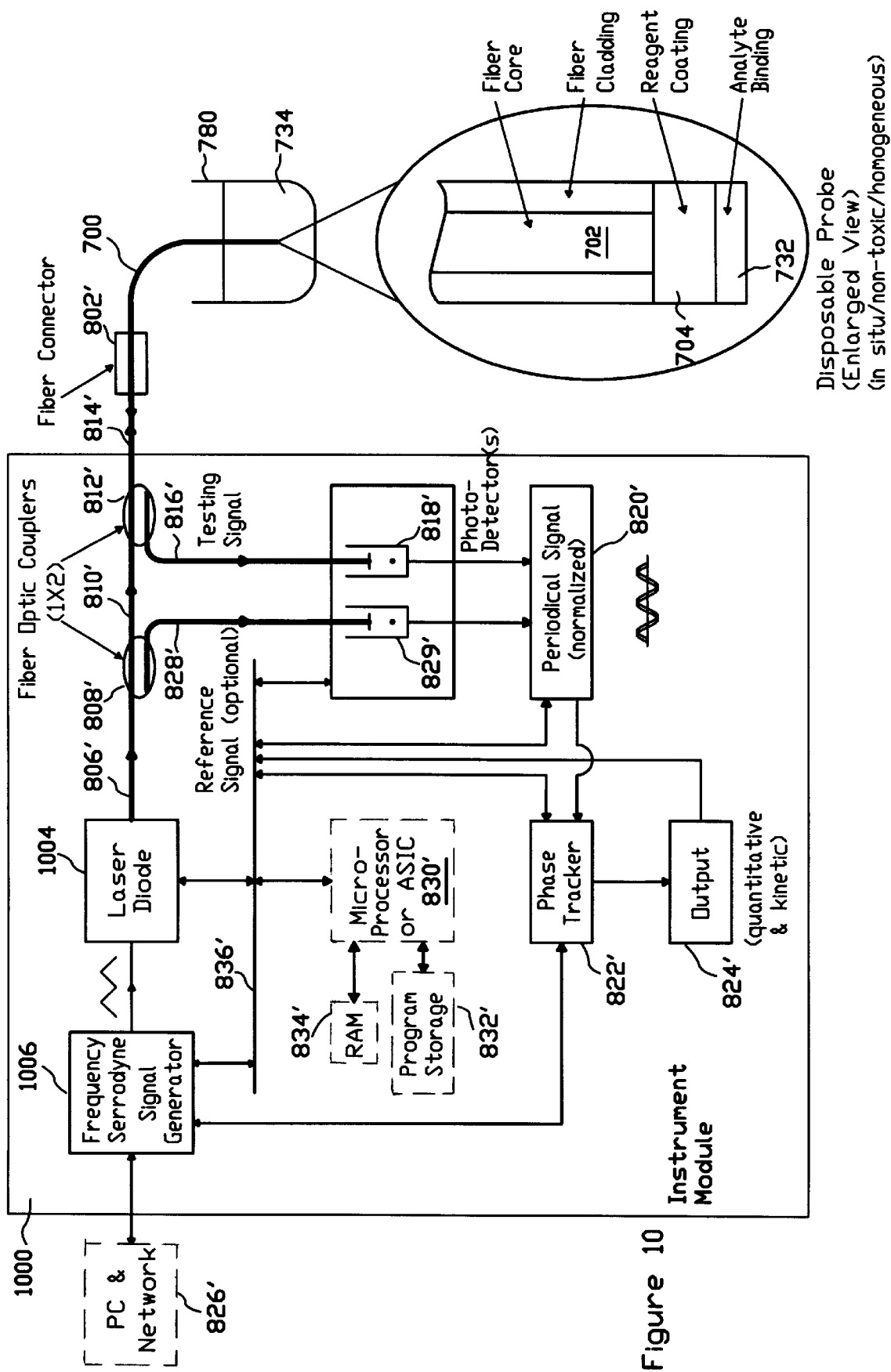
FIG. 10 is a schematic of a second embodiment of the biosensor of my invention.

FIG. 10 is a schematic of a second embodiment of my biosensor. The second embodiment of my biosensor includes a modified biosensor optical analyzer 1000. Most elements are the same as shown in FIG. 8 except: (i) the broadband light source 804 is replaced with a laser diode 1004 driven by a frequency serrodyne signal generator 1006; and (ii) the phase tracker 822' now must be synchronized with the frequency serrodyne signal generator 1006. The frequency serrodyne signal generator produces a ramped frequency (or "chirp") drive signal. The operation of this embodiment is otherwise similar to the first embodiment described above with reference to FIG. 8. However the phase tracker 822' must be synchronized with the frequency serrodyne signal generator 1006. Further multi-mode optical fiber must be used as the optical waveguides 806', 810', 814', 816', and 828'.

Figure 11:
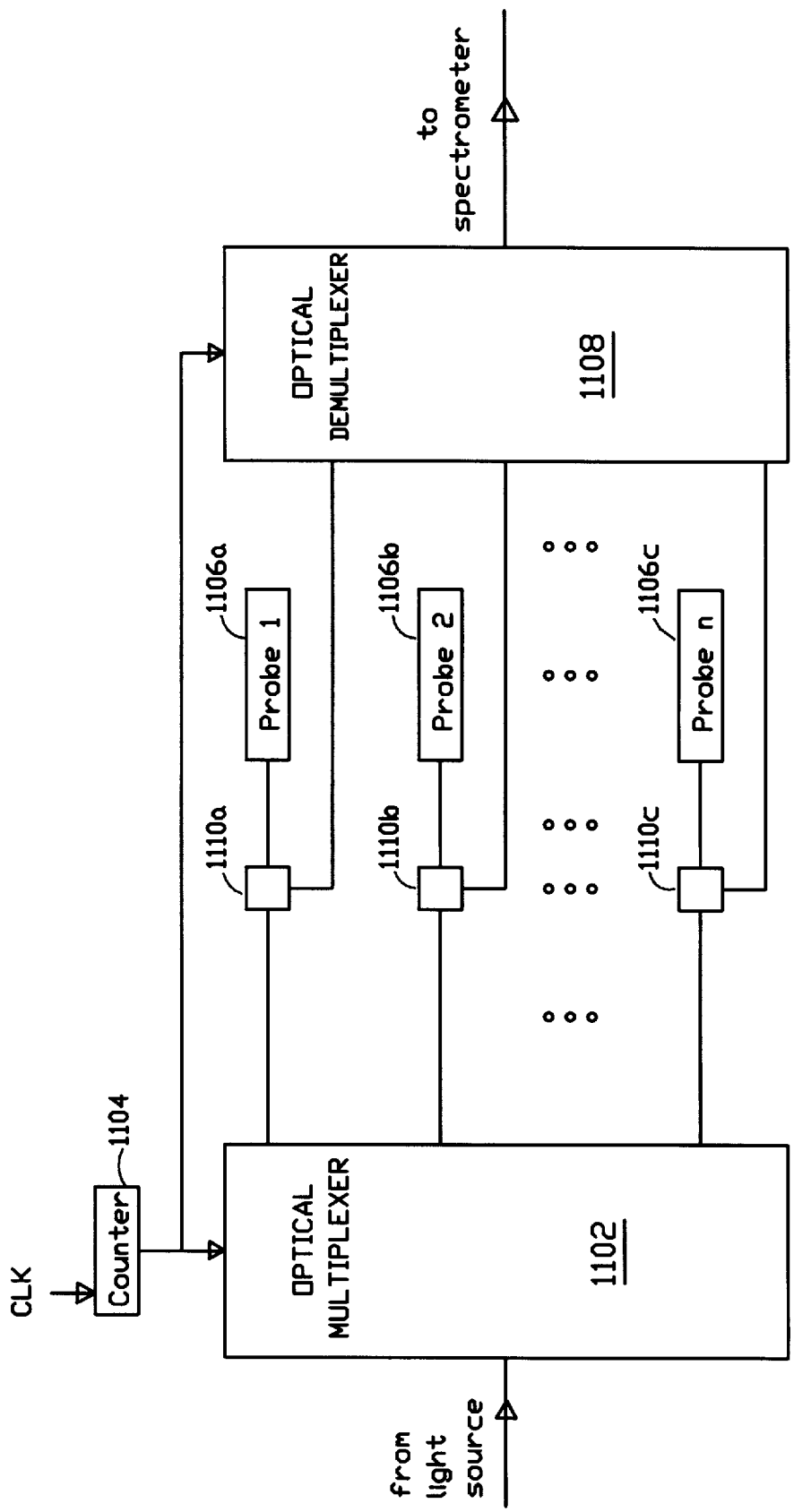
FIG. 11 is a block schematic illustrating a way of multiplexing the biosensor of my invention.

Since the bioprobe 700 of my invention is relatively small and permits remote, real time testing, multiplexing more than one (1) bioprobe to detect different substances in a solution is feasible. FIG. 11 illustrates an example of multiplexing more than one bioprobe. As shown in FIG. 11, an optical multiplexer 1102 receives, at its input, a light beam (such as a fixed frequency light beam) from a light source (not shown). The optical multiplexer 1102 switches the input through to one of N outputs in accordance with an input control signal. This input control signal may be provided by a clocked counter 1104, for example. One or more of the N outputs of the optical multiplexer 1102 are coupled via waveguides and connectors 1110 with one or more bioprobes 1106. Each of the one or more bioprobes 1106 is coupled, via the connectors 1110, with an associated input of an optical demultiplexer 1108. The connectors 1110 may be similar to the 2-by-1 or Y connectors discussed above. Based on a control input signal, the optical demultiplexer 1108 supplies one of its N inputs to a spectrometer (not shown). Although this example shows a time division multiplexing device, frequency division multiplexing is also feasible as will be apparent to those skilled in the art.

In view of the above description, my improved biosensor has a simple structure which permits a low cost, disposable, probe. Due to its small size, multiple assays may be performed simultaneously and in vivo testing is feasible. Further, my biosensor operates without unstable and potentially toxic labels or indicators. Furthermore, my biosensing system permits continuous data acquisition, as well as end-point data acquisition and real time data analysis. Since data measurements are communicated optically, my biosensing system is electrically isolated from a patient thereby permitting safe in vivo testing. Since my biosensing system uses a bioprobe in an overlook arrangement with respect to the sample solution, non-specific bondings are minimized. Since my biosensing method exploits Fresnel's law, it is highly sensitive has exhibited a large linear range.

What is claimed is:

1. A method of determining the concentration of a substance in a sample solution, using a fiber optic probe having a reagent at its distal end to which the substance bonds, the method comprising steps of:
   a) immersing the distal end of the fiber optic probe into the sample solution;
   b) optically coupling a light source with a proximal end of the fiber optic probe;
   c) detecting a first light beam, and a second light beam, reflected at the distal end of the fiber optic probe;
   d) detecting an interference pattern formed by the first and second light beams at a first time;
   e) detecting an interference pattern formed by the first and second light beams at a second time; and
   f) determining whether the substance is present in the sample solution based on whether a shift occurs in the interference patterns.

2. The method of claim 1 further comprising a step of determining a concentration of the substance based on a shift in the interference patterns and based on a differential between the first and second times.

3. The method of claim 1 wherein each step of detecting includes sub-steps of:
   i) dispersing an interference beam, formed by the first and second light beams, onto a spectrometer to form a spectral dispersion pattern;
   ii) determining a periodic function based on the spectral dispersion pattern; and
   iii) determining a phase of the periodic function.

4. The method of claim 1 further comprising a step of:
   modulating the frequency of the light source optically coupled with the proximal end of the fiber optic probe,
   wherein the step of determining whether the substance is present in the sample solution based on whether a shift occurs in the spectral patterns is synchronized with the frequency of the light source.

5. The method of claim 1 wherein the first time is before a reaction of the substance and the reagent layer and the second time is after the reaction of the substance and the reagent layer.

6. The method of claim 1 wherein the first and second times occur during a reaction of the substance and the reagent layer.

7. The method of claim 1 wherein the second time approaches the first time thereby allowing continuous monitoring.

8. A system for detecting the concentration of a substance in a sample solution, the system comprising:
   a) a light source for providing a light beam;
   b) a fiber optic probe including a fiber optic section having a proximal end for receiving an incident light beam and a distal end tip, and a reagent layer immobilized on the distal end tip, the fiber optic probe for producing at least a first reflected beam and a second reflected beam from the incident light beam;
   c) a detector for detecting an interference pattern formed by the first and second reflected beams;
   d) a coupler for optically coupling the light source with the fiber optic probe and for optically coupling the fiber optic probe with the detector; and
   e) a processor for determining a phase associated with an interference pattern detected by the detector at a first time and for determining a phase associated with an interference pattern detected by the detector at a second time and for determining the concentration of the substance based on a shift in the phases associated with the interference patterns detected by the detector at the first and second times.

9. The system of claim 8 wherein the detector is a spectrometer.

10. The system of claim 8 wherein the detector is a one-dimensional charge coupled device.

11. The system of claim 8 wherein the detector is a 1×1024 charge coupled device.

12. The system of claim 8 wherein the processor includes:
    i) a periodic signal interpreter/generator for generating a first periodic signal based on the interference pattern detected by the detector at the first time and a second periodic signal based on the interference pattern detected by the detector at the second time;
    ii) a phase tracker for determining a phase of the first periodic signal and a phase of the second periodic signal; and
    iii) a computer for computing a phase difference between the phases of the first and second periodic signals and for determining the concentration of the substance in the sample solution based on the phase difference.

13. The system of claim 8 wherein the coupler is a "Y" coupler.

14. The system of claim 8 wherein the light source is a broadband light source.

15. The system of claim 8 wherein the light source is a tunable laser diode.

16. The system of claim 8 further comprising a frequency modulator, coupled with the light source, for modulating the frequency of the light beam provided by the light source.

17. The system of claim 16 wherein the processor is synchronized with the frequency modulator.

18. The system of claim 8 further comprising:
    a second fiber optic probe for determining the concentration of a second substance in the sample solution;
    an optical multiplexer, coupled between the light source and each of the fiber optic probe and the second fiber optic probe, for optically coupling the light source with one of the fiber optic probes in a time division manner; and an optical demultiplexer, coupled between each of the fiber optic probes and the detector, wherein the optical multiplexer and the optical demultiplexer are synchronized with respect to each other such that only one of the fiber optic probes may be actively coupled with both the light source and the detector at any time.

19. The system of claim 8 wherein the first time is before a reaction of the substance and the reagent layer and the second time is after the reaction of the substance and the reagent layer such that the processor is provided with end point data.

20. The system of claim 8 wherein the first and second times occur during a reaction of the substance and the reagent layer.

21. The system of claim 20 wherein the second time approaches the first time thereby allowing continuous monitoring.

* * * * *